United States Patent [19]

Trogler et al.

[11] Patent Number: 4,684,751

[45] Date of Patent: Aug. 4, 1987

[54] CATALYTIC COMPOSITIONS FOR PREPARING AMIDES AND PRIMARY ALCOHOLS

[75] Inventors: William C. Trogler, Encinitas; Craig M. Jensen, San Diego, both of Calif.

[73] Assignee: The Regents of the University of California, Berkeley, Calif.

[21] Appl. No.: 829,410

[22] Filed: Feb. 13, 1986

[51] Int. Cl.$^4$ .................... C07C 29/04; C07C 31/125; C07C 31/20

[52] U.S. Cl. .................................. 568/898; 502/162; 556/23; 564/128; 568/852

[58] Field of Search ................................ 568/898, 852

[56] References Cited

U.S. PATENT DOCUMENTS

| | | | |
|---|---|---|---|
| 2,051,144 | 8/1936 | Joshua et al. | 568/898 |
| 2,052,095 | 8/1936 | Joshua et al. | 568/898 |
| 3,816,550 | 6/1974 | Young et al. | 568/898 |
| 3,966,798 | 6/1976 | Intille et al. | 260/486 R |
| 3,988,381 | 10/1976 | Dulog | 568/898 |
| 3,992,456 | 11/1976 | Atkins et al. | 568/898 |
| 4,177,210 | 12/1979 | Vanderkooi et al. | 260/561 N |
| 4,322,532 | 3/1982 | Braithwaite | 546/128 |
| 4,329,500 | 5/1982 | Habermann | 564/128 |

OTHER PUBLICATIONS

Article by Arnold and Bennett in Journal of Organometallic Chemistry, vol. 199 (1980), pp. 119–135.
Article by Villain, Gaset and Kalck in Journal of Molecular Catalysis, vol. 12 (1981), pp. 103–111.

Primary Examiner—J. E. Evans
Attorney, Agent, or Firm—Brown, Martin, Haller & Meador

[57] ABSTRACT

A catalytic composition useful for producing amides and primary alcohols from nitriles and alkenes respectively, comprising in the first instance water, a suitable nucleophile, and $MHCl[P(R)_3]_2$ wherein M is platinum, palladium, or nickel, and R is $CH_3$, $CH_3 CH_2$, or i-Pr and in the second instance comprising the same reagents but limited to R being $CH_3$. The addition of a phase-transfer catalyst facilitates both reactions where the aqueous solubility of the nitriles or alkenes is limiting in the reaction.

7 Claims, 3 Drawing Figures

CATALYTIC COMPOSITIONS FOR PREPARING AMIDES AND PRIMARY ALCOHOLS

This invention was made with Government support under Grant No. DAAG29-83-K-0175 with the U.S. Army Research Office and the University of California. The Government has certain rights in this invention.

BACKGROUND OF THE INVENTION

Described herein are catalytic compositions capable of converting nitriles to amides, and alkenes to primary alcohols.

A general procedure for obtaining carboxamides [RC(O)NH$_2$] is to effect hydration of the corresponding nitriles with suitable acid or base catalysts. This is shown in the following equation:

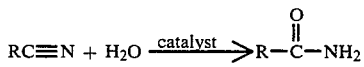

A carboxamide of considerable commercial importance is acrylamide. The latter is utilized in polymer form in paper production, waste water recovery, as well as oil recovery processes, and is favorably employed in numerous other commercial applications. Because of undesirable competing side reactions arising from the use of heterogenous catalysts such as reduced copper metal oxides there is presently considerable effort directed toward identifying catalysts capable of effecting regioselective hydrolysis of acrylonitrile to yield acrylamide. For example, homogeneous catalysts consisting of noble metals, particularly platinum, yield mixtures of chemicals derived from the reaction with acrylonitrile. The following equation reveals that hydration of acrylonitrile with a conventional platinum catalyst yields acrylamide, beta-cyanoethanol, and beta-dicyanoethylether:

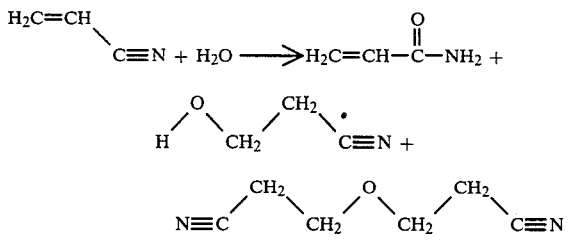

Hydration of the unsaturated double bond associated with acrylonitrile produces beta-cyanoethanol, while beta-dicyanoethylether results from the addition reaction of the hydroxyl group on beta-cyanoethanol to the double bond of acrylonitrile. Attempts to prevent the formation of undesirable side products have met with limited success.

An additional undesirable feature associated with the catalytic conversion of amides from nitriles is the necessity to perform the reaction at elevated temperatures. For example, Arnold and Bennett, in the *Journal of Organometallic Chemistry*, (1980, 199:119-135), show several platinum and palladium organo tertiary phosphine compounds with appreciable catalytic activity only at temperatures above 80° C.

A second class of nitriles that are difficult to hydrate using conventional synthetic schemes are those that display an ester functionality. Members of this class, including precursors to pyridones, are chemical intermediates useful for preparing a variety of medicinals. Thus, it is desirable to discover alternative methods of generating these compounds.

It is apparent from the foregoing discussion that it is desirable to have a catalyst that converts nitriles to amides without the production of significant side products, and moreover, that functions adequately at low temperatures.

There are numerous other chemical reactions where the commercial feasibility of obtaining the products derived therefrom would be greatly increased if suitable catalysts were available. An example is the hydration of terminal unsaturated double bonds associated with various classes of hydrocarbon molecules. A specific instance whereby such catalysts would be useful is the hydration of alkenes to produce primary alcohols. While catalysts such as phosphoric acid, transition metal oxides, zeolites, and clays do catalyze the hydration of alkenes, the products are generally not primary alcohols because the reactions follow Markownikoff's rule, or if they are produced at all, the yields are too low to be commercially appealing. Antimarkownikoff addition reactions are known such as hydroboration, but these are not catalytic.

Because straight-chain primary alcohols have extensive commercial use, particularly in surfactants, plasticizers, and the like, it would be commercially advantageous to have catalysts capable of producing these substances selectively, and under mild reaction conditions.

SUMMARY OF THE INVENTION

The noble transition metal-based tertiary trimethyl, triethyl, and tri-i-propyl phosphine compounds are described that catalyze the conversion of a wide variety of nitriles to amides. The compounds are particularly useful for obtaining acrylamide from acrylonitrile. The catalysts differ significantly from other noble metal-based organo tertiary phosphine complexes as they are functional at lower temperatures and exhibit higher rates of catalysis. Indeed, the tertiary trimethylphosphine compound exhibits high catalytic activity at temperatures only slightly greater than room temperature, and regioselectively converts acrylonitrile to acrylamide in 96% yields. Both the triethyl and trimethyl phosphine compounds are additionally capable of regioselective hydration of compounds exhibiting both ester and nitrile moieties. The noble transition metal-based tertiary trimethyl phosphine compound is also useful for generating primary alcohols from alkenes, as well as generally being useful to hydrate double bonds associated with various classes of hydrocarbons via anti-Markownikoff addition. In those cases where either the nitrile or the alkene is poorly soluble in aqueous solution, the reaction is carried out in a two-phase system with the aid of a phase-transfer catalyst.

Figure 1:
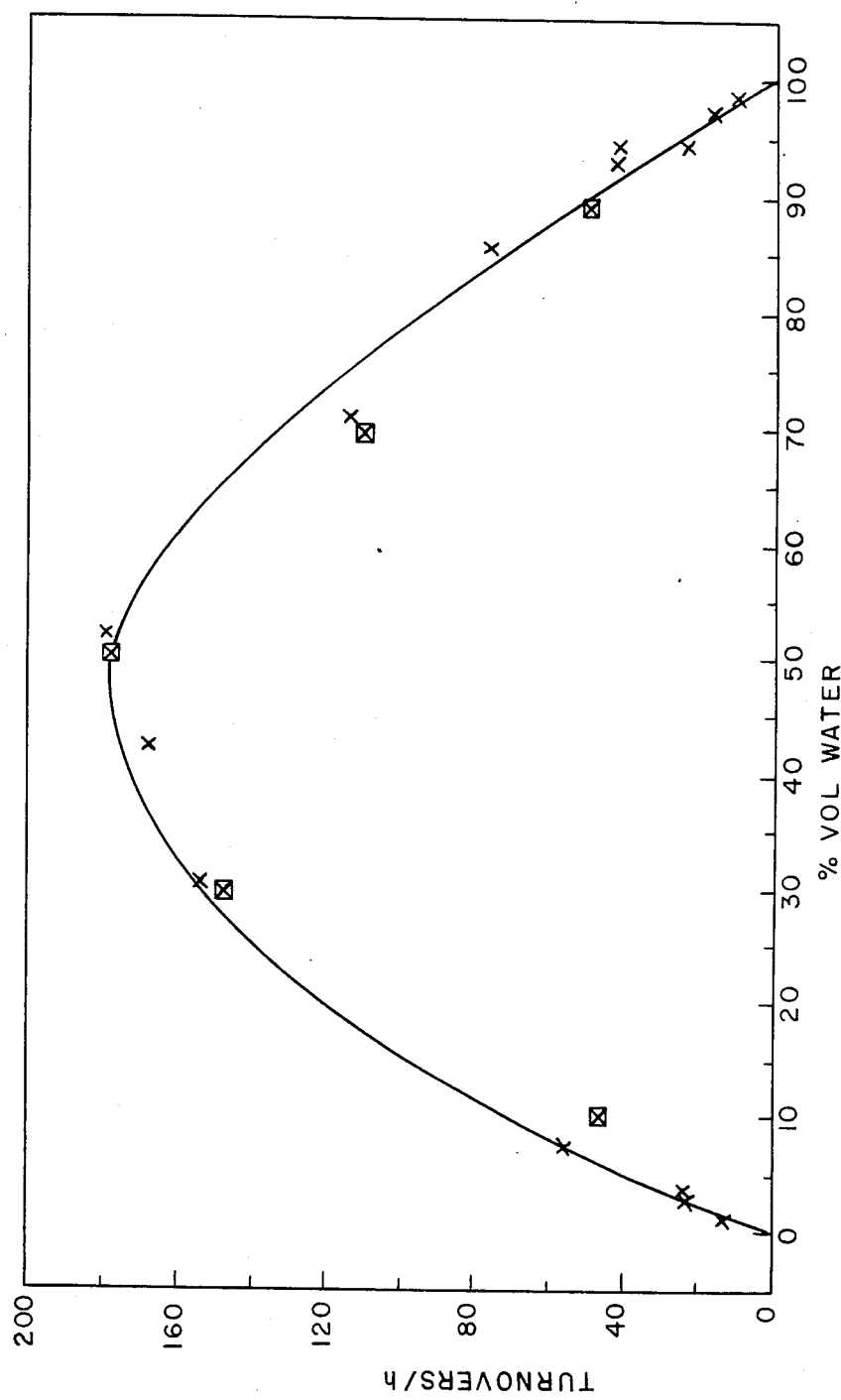
FIG. 1 represents the conversion of acetonitrile to acetamide as a function of the water concentration. The reaction is carried out in the presence of trans-PtHCl(PMe$_3$)$_2$. X represents actually determined experimental values, while $\boxed{X}$ represents theoretical values.

TABLE I presents the catalytic activities for the hydrolysis of acetonitrile to acetamide for the PMe$_3$ analogue, as well as for other catalysts.

TABLE II presents the rate of hydration of acetonitrile to acetamide with varying trans-PtHCl(PMe$_3$)$_2$ concentrations.

TABLE III shows the effect of varying the water concentrations on the rate of production of acetamide from acetonitrile when the PMe$_3$ analogue is utilized.

TABLE IV shows the rate of acetamide production as a function of hydroxide ion concentrations when the PMe$_3$ analogue is used.

TABLE V displays the amount of acetamide produced at different time periods when the platinum PMe$_3$ complex is the catalyst.

TABLE VI shows the rate and product distribution when acrylonitrile is converted to acrylamide in the presence of the platinum PMe$_3$ complex catalyst.

TABLE VII shows the effect of varying water concentrations on the products obtained from the hydration of acrylonitrile when the platinum PMe$_3$ complex is the catalyst.

TABLE VIII compares the product distribution obtained from the hydrolysis of acrylonitrile when the platinum PMe$_3$ complex is used as catalyst and the reaction is conducted at 25° C. and 80° C.

TABLE IX shows the rate of conversion of acetonitrile to acetamide in the presence of the PEt$_3$ analogue.

TABLE X displays the rate data for the hydration of acetonitrile to acetamide as a function of hydroxide ion concentration when the platinum PEt$_3$ complex is the catalyst.

TABLE XI shows the rates and extent of conversion of several nitriles to amides and pyridones.

DETAILED DESCRIPTION OF THE INVENTION

It is important to note that while the properties of the invention catalyst are described in terms of a few reactions wherein a limited number of either nitriles or alkenes are catalyzed to amides or primary alcohols respectively, the scope of their catalytic applicability is not to be construed so narrowly. It is to be anticipated that the invention catalyst are effective on nitriles and alkenes generally as classes of substrates.

Trans-PtHcl(PMe$_3$)$_2$ was prepared as described by Packett et al. in the *The Journal of Inorganic Chemistry* (1985, 24:3578–3583). This involves combining trimethyl phosphine in an inert atmosphere with a solution of cis-PtCl$_2$(SEt$_2$)$_2$. The latter compound was prepared as described by Kauffmann and Cowan in *Inorganic Synthesis*, (1960, 6:211–215) and was dissolved in CH$_2$Cl$_2$. On addition of trimethyl phosphine a white solid precipitates from solution. The solvent was subsequently removed in vacuo, and the solid was washed with a suitable organic solvent, particularly ether, and then dried under vacuum to remove excess trimethyl phosphine. The solid was recrystallized, yielding cis-PtCl$_2$(PMe$_3$)$_2$ in about 70% yield.

Cis-PtCl$_2$(PMe$_3$)$_2$ was added to a flask, the latter flushed with nitrogen, and deoxygenated tetrahydrofuran (THF) added. The resulting suspension was cooled, and the reactants exposed to hydrogen gas for several minutes. Next, sodium naphthalide was added, and the hydrogen gas stream maintained. Residual PtH$_2$(PMe$_3$)$_2$ was removed, the solution filtered, and the filtrate concentrated and overlaid with pentane. Next, the solution was cooled for several hours, at which time colorless crystals separated from solution. Analysis showed that the crystals were trans-PtHCl(PMe$_3$)$_2$.

Trans-PtHCl(PEt$_3$)$_2$ was prepared as described above with the exception that triethyl phosphine was substituted for trimethyl phosphine.

The catalytic activity of trans-PtHCl(PMe$_3$)$_2$ catalyzes the conversion of nitriles to amides in the presence of a suitable nucleophile, particularly hydroxyl ions. The reaction is carried out in an aqueous solution, and the rate of reaction is a function of the amount of water present. FIG. 1 shows the dependency of the rate on the percent-volume water present when the reaction is carried out at 80° C. It is apparent that the maximal rate occurs in the range of about 40%–50% water.

An undesirable side reaction associated with the hydration of the nitrile groups generally, and acrylonitrile, specifically, is the simultaneous hydration of the olefinic group. Indeed, when the reaction is carried out at 80° C., significant amounts of beta-cyanoethanol and beta-dicyanoethylether are produced. We have now found that the production of these undesirable side products can be nearly completely eliminated by carrying out the catalytic event at lower temperatures. It is particularly advantageous to run the reaction at near room temperature, or about 25° C. At this temperature trans-PtHCl(PMe$_3$)$_2$ exhibits remarkable regioselective catalytic activity and yields about 97% acrylamide.

The catalyst, trans-PtHCl(PEt$_3$)$_2$, is also favorably employed in an oxygen-free solution to produce acrylamide from acrylonitrile. Initiation of catalysis is facilitated by heating the mixture to 75° C. after adding the nucleophilic reagent, or by prior removal of the chloride ligand with AgPF$_6$ by procedures well-known to those in the art. The rate of conversion of acrylonitrile to acrylamide is substantially lower for trans-PtHCl(PEt$_3$)$_2$ than for the analogous PMe$_3$ catalyst.

Figure 2:
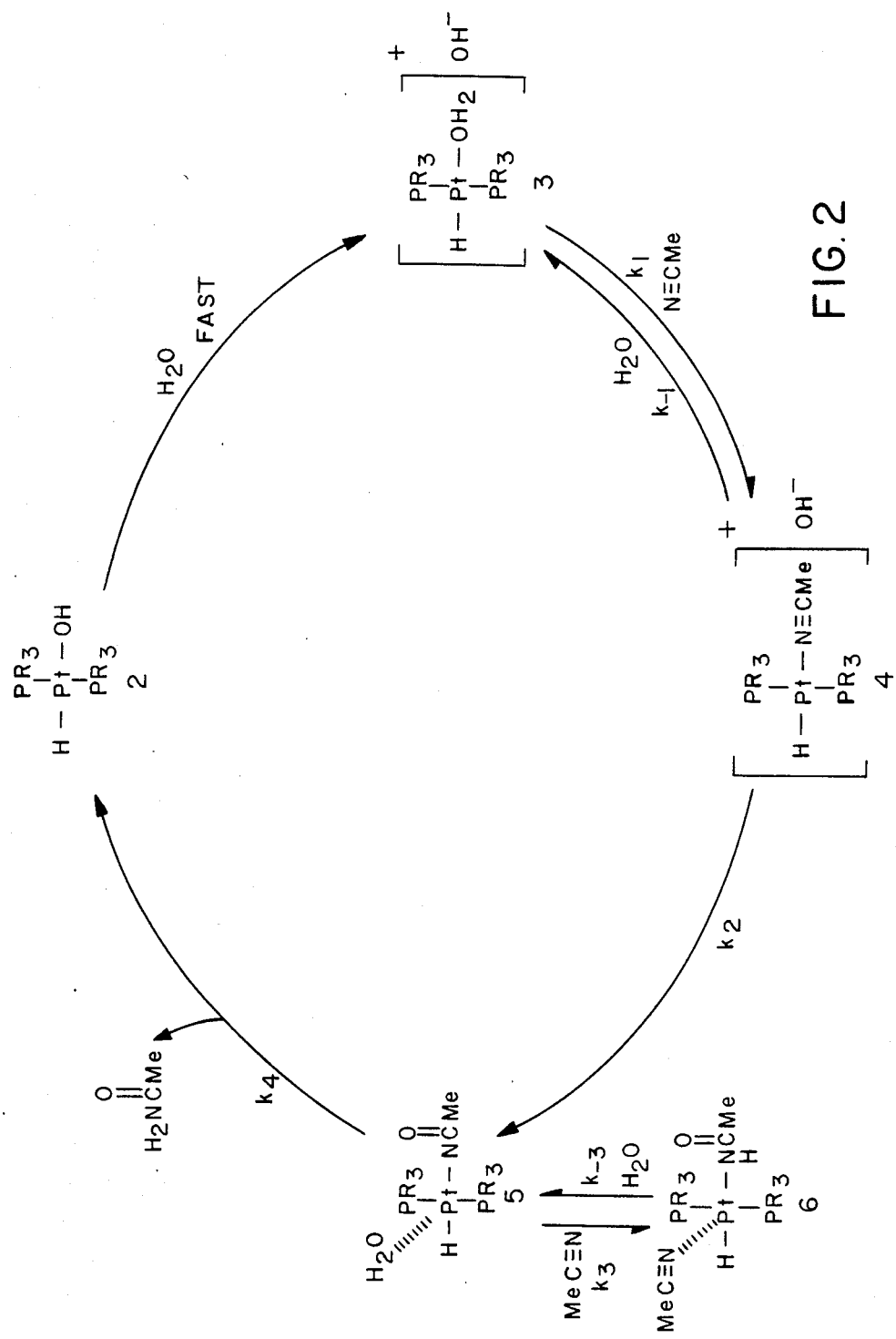
FIG. 2 shows the catalytic cycle for the conversion of nitriles to amides for either the PEt$_3$ or PMe$_3$ analogues.

Mechanistic studies reveal that trans-PtHCl(PMe$_3$)$_2$ and trans-PtHCl(PEt$_3$)$_2$ interact with the reagents in solution to form catalytic intermediates that are involved in the overall catalytic event. Applicants do not wish to be bound by any particular theory as to mechanism. FIG. 2 shows what is believed to be the catalytic cycle for the conversion of nitriles to amides for either the PEt$_3$ or PMe$_3$ analogue. The scheme depicts the conversion of a typical nitrile, acetonitrile, to acetamide. Complex (2) shows the platinum catalyst after displacement of chloride by hydroxyl ions, and in the presence of water a proton is abstracted by the coordinated hydroxyl group yielding complex (3). The subsequent steps involve the substitution of platinum-bound water by acetonitrile to yield complex (4) and the nucleophilic attack of hydroxide ion on coordinated nitrile to produce (5). Finally, the catalytic cycle is completed with the substitution of the N-carboxamido group by hydroxide, and the generation of acetamide and the regeneration of the catalytic starting material, either PEt3 or the PMe$_3$ analogues.

It is apparent from the catalytic scheme presented supra that the complex first generated is [trans-ptH(H$_2$O)(PR$_3$)$_2$]OH, where R is either Et or Me. While this complex is conveniently generated from trans-PtHCl(PMe$_3$)$_2$, it is to be anticipated that analogous catalysts such as [trans-PtH(OH$_2$)(PMe$_3$)$_2$]PF$_6$ can also be utilized in the presence of one equivalent of sodium hydroxide. The latter compound is generated as described by Clark and Jablonski in *Inorganic Chemistry* (1974, 13:2213).

In addition to the nitriles described above, the subject catalysts are capable of converting nitriles that exhibit ester linkages to their corresponding amides or, in appropriate cases, pyridones. Thus, catalytic solutions were prepared under nitrogen to effect the hydration of methyl cyanoacetate, ethyldicyanomethylmethylenebutyrate, and 1,1-dicyano-2-methylpent-1-ene. The solutions contained one equivalent of NaOH per equivalent of platinum to a solution containing the nitrile of interest and the appropriate catalyst. Further, a phase-transfer catalyst considerably enhances the reaction in those instances where the nitrile is relatively insoluble in the aqueous solution. The reactions were conducted at 78° C. in an inert atmosphere in sealed ampoules. After a suitable reaction period, products were isolated and analyzed by standard techniques. It was observed that methyl cyanoacetate is converted to methylacetamidate in about 91% and 94% yields when the PEt3 and PMe3 analogues are utilized, respectively.

Additionally, ethyldicyanomethylmethylenebutyrate is converted to 3-cyano-6-hydroxy-2-keto-4-methylpyridone in 40% and 88% yields when the PEt3 and PMe3 analogues are used, respectively. Further, 1,1-dicyano-2-methylpent-1-ene is converted to E-2-cyano-3-methylhex-2-ene-amide in a 64% yield when the PMe3 analogue is used. A similar result is expected when the PEt3 analogue is employed. Finally, 2,6-diketopiperidine was converted to 3-cyano-6-hydroxypyridone in 72% yield when PMe3 is used as catalyst. No conversion is observed when PEt3 is utilized.

As alluded to supra, the invention catalysts are capable of catalyzing the hydrolysis of olefins. While this reaction is an undesirable side reaction in the conversion of nitriles to amides, it is particularly useful in generating primary alcohols from alkenes. Further, it should be noted that it is not limited solely to alkenes and can be favorably employed to hydrate via anti-Markownikoff addition olefinic linkages generally, particularly when the double bond is separated from other reactive groups (i.e., OH) by two or more $CH_2$ groups. The reaction is typically carried out in a two-phase system consisting of water, alkene, nucleophilic reagent, particularly hydroxide ions, the PMe3 analogue catalyst, and a phase-transfer catalyst. The reaction is oxygen-sensitive; thus for maximum efficiency, it is desirable that the solution be deoxygenated and the reaction effected in an airtight vessel. Analysis of the reaction products by gas chromography revealed that approximately 96% of the alkene was converted to the corresponding primary alcohol. In contrast to palladium (II) catalysts used by others, trans-PtHCl(PMe3)2 does not yield aldehyde side products. Here again, Applicants do not wish to be bound by any particular theory as to mechanism.

Figure 3:
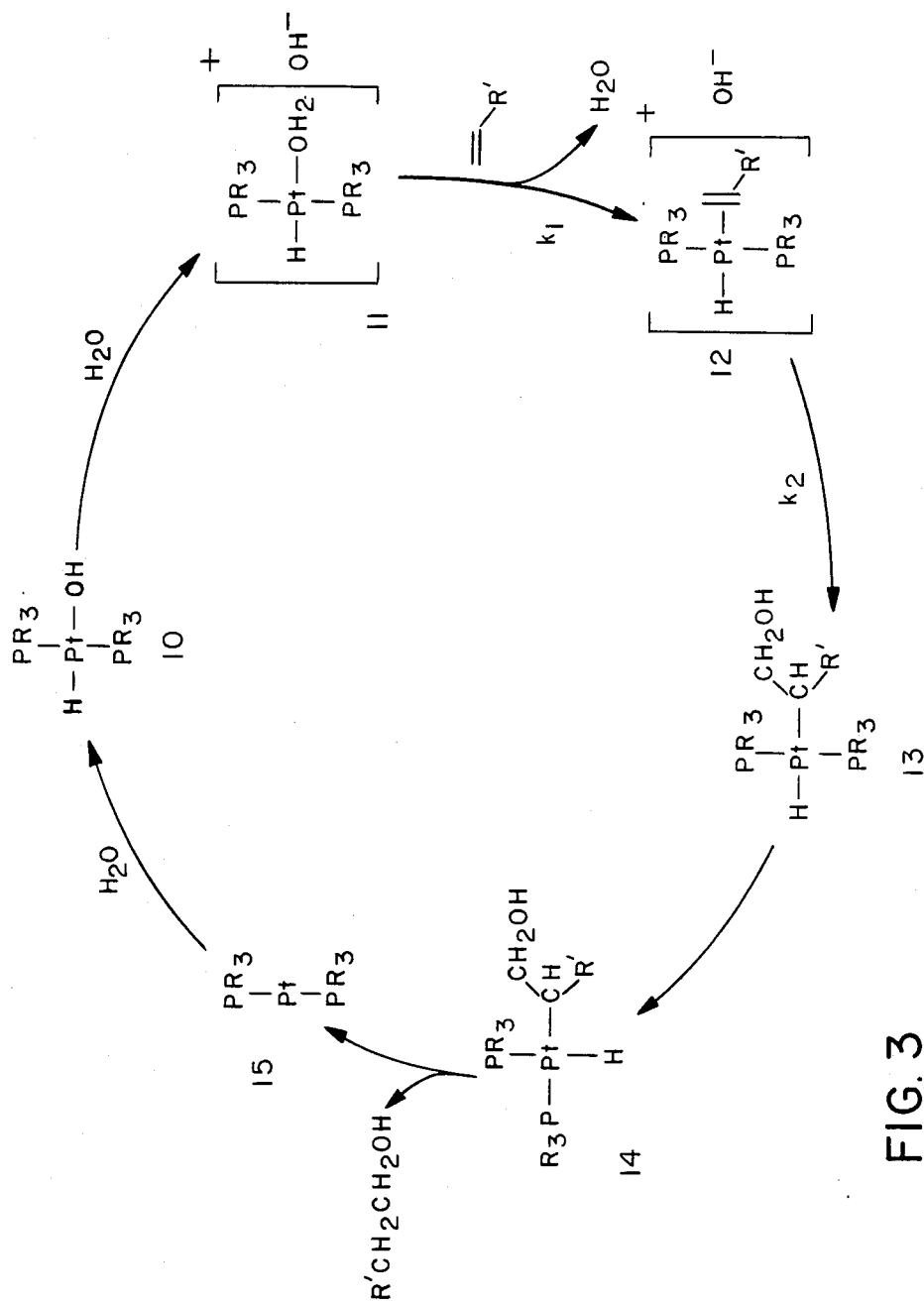
FIG. 3 shows the catalytic cycle for the conversion of alkenes to primary alcohols in the presence of trans-PtHCl(Me$_3$)$_2$.

Similar to the catalytic conversion of nitriles to amides, the complex first generated in the production of primary alcohols from alkenes is [trans-PtH(H2O)(PMe3)2]OH. Generation of this complex is shown in FIG. 3 and results from the displacement of chloride via hydroxide ions. The figure also shows what are believed to be subsequent steps in the reaction scheme. Platinum-bound water is substituted by the alkene to yield complex (12), which on nucleophilic attack of the coordinated alkene by hydroxide ion yields complex (13). Complex (13) generates the primary alcohol and reestablishes the catalytic cycle.

Several features of the reaction scheme are noteworthy. As already mentioned supra, aldehyde products are not generated using the PMe3 analogue. Presumably this is because the size of the PMe3 ligand allows rapid cis-trans isomerization (14) and reductive elimination of alcohol product before beta elimination can result in aldehyde formation. Second, turnover rates for lower hydrocarbon alkenes are in the range 7–20 turnovers/hour at 100° C.

The following examples are given to aid and understand the invention, but it will be understood by those skilled in the art that the invention is not to be so limited to the particular procedures, conditions, or materials of the example.

EXAMPLES

Example 1

Preparation of trans-PtHCl(PMe3)2 or trans-PtHCl(PEt3)2.

1.6 ml, or 16 mMoles of either trimethylphosphine or triethylphosphine was added dropwise under nitrogen to a stirred solution of cis-PtCl2(SEt2)2 as described by Kauffmann and Cowan in *Inorganic Synthesis*, supra. 3.2 gms, or 7.2 mMoles of the latter reagent was dissolved in a minimal amount of $CH_2Cl_2$. A white solid precipitated from the yellowish solution, and the solvent was removed in vacuo. The solid was washed with diethyl ether and dried under vacuum to remove excess PMe3 or PEt3. Recrystallization of the precipitate was accomplished using ethanol and then dissolved in diethylether. Approximately 2.1 gms of cis-PtCl2(PMe3)2 and cis-PtCl2(PEt3)2 was obtained. Infrared spectral determinations as well as nuclear magnetic spectroscopy ($^1H,^{31}P$), confirmed the chemical identity of the molecules. 0.2 gms, or 0.48 mMoles of cis-PtCl2(PMe3)2 or cis-PtCl2(PEt3)2 was dissolved in a Schlenk flask in 5 ml of dry deoxygenated tetrahydrofuran. The flask was flushed with nitrogen, and the resulting suspension cooled to 0° C. A stream of hydrogen gas was bubbled through the suspension for 5 minutes, after which one equivalent of sodium naphthalide was added dropwise with vigorous stirring, and the hydrogen purged maintained during the addition. The solution exhibited a colorless-to-yellow appearance, which upon filtration through activated charcoal and Celite ® yielded a colorless solution. The filtrate was concentrated to 1ml under-vacuum, and 5 ml of pentane was layered on top. After the solution had cooled to −20° C. for 10 hours, wellformed, colorless crystals were apparent. The supernatant was removed to yield approximately 0.21 gms of trans-PtHCl(PMe3)2 or trans-PtHCl(PEt3)2. J. Chatt and B. L. Shaw, J. Chem. Soc. (1962), page 5075.

EXAMPLE 2

Production of acetamide from acetonitrile with trans-PtHCl(PMe3)2

The conversion of acetonitrile to acetamide is described as one example of the conversion of nitriles to amides. A catalytic solution consisting of trans-PtHCl(PMe3)2, one equivalent of NaOH in a solution with equal amounts of acetonitrile and water effects the hydration of acetonitrile at a rate of approximately 20 turnovers/hour at 25° C., and considerably greater than that at elevated temperatures. As the reaction is sensitive to oxygen, it must be performed in an inert atmosphere, nitrogen being suitable for this purpose. Products were analyzed after a suitable reaction period using gas chromographic techniques well-known to those in the art. Table I presents the catalytic activities for the hydrolysis of acetonitrile to acetamide for the $PMe_3$ and analogues, as well as the temperatures at which the rate was measured. In addition, for comparison purposes a number of other complexes and their catalytic activities are presented.

To further characterize the catalysis of nitriles to amides, the effect of varying the concentration of the reactants as well as the rate of the reaction were determined. Table II presents the rate of hydration of acetonitrile to acetamide with varying trans-$PtHCl(PMe_3)_2$ concentrations when the reaction is carried out at 80° C. It is apparent that the reaction rate is linear under these conditions.

Table III shows the effects of varying the water concentration on the rate of production of acetamide from acetonitrile when the $PMe_3$ analogue is utilized. It is apparent that at both low- and high-water concentrations the rate of reaction is greatly reduced, whereas the maximum rate of reaction is in the range of about 30%–70% water.

Table IV shows the effect of varying the hydroxyl ion concentration on the rate of the reaction. At low hydroxyl-ion concentrations, the rate is nearly linear; whereas with increasing concentrations, the rate becomes independent of the hydroxide-ion concentration.

Last, Table V shows that the production of acetamide is linear over a time period of 240 hours.

EXAMPLE 3

Catalytic conversion of acrylonitrile to acrylamide with trans-$PtHCl(PMe_3)_2$

Similar studies were carried out on the conversion of a second nitrile, acrylonitrile, to an amide, acrylamide, to further characterize the catalytic properties of trans-$PtHCl(PMe_3)_2$. The rate of production of acrylamide, as well as by-products produced in the reaction as a function of hydroxide ion and water concentration, are shown in Tables VI and VII, respectively. It is important to note that the date presented in these tables was gathered at about 78°–80° C. Consequently, while there is considerable amount of acrylamide produced, the by-products are also generated in significant amounts. Further, note that at low hydroxide-ion concentrations the reaction rate for the production of acrylamide is nearly independent of the hydroxide-ion concentration. Also, note that similar to the reaction wherein acetamide is produced from acetonitrile, the catalytic reaction involving the generation of acrylamide is dependent on the amount of water present. The reaction rate is most appreciable at between 30%–60% water and proceeds less rapidly at lower and higher water concentrations. The concentration of hydroxide ion present in the reactions shown in Table VI was 0.02 M.

A key catalytic property of trans-$PtHCl(PMe_3)_2$ is its capacity to effect considerable catalytic conversion of nitriles to amides at low temperatures with little or none of the by-products produced at higher temperatures. Table VIII shows that there is virtually no beta-cyanoethanol produced and little beta-dicyanoethylether. In contrast, at 80° C., an amount of beta-cyanoethanol equal to or greater than acrylamide is produced, as well as a considerable amount of the ether.

EXAMPLE 4

Synthesis of acetamide from acetonitrile using trans-$PtHCl(PEt_3)_2$ as catalyst The capacity of trans-$PtHCl(PEt_3)_2$ to effect production of acetamide from acetonitrile was examined. Table IX shows that at 80° C. the generation of acetamide is nearly linear over the range 0.25–2.00 equivalents of the $PEt_3$ catalyst. The concentration of hydroxide ion present was 0.02M. For comparative purposes FIG. 1 shows moles of acetamide produced per moles of either trans-$PtHCl(PEt_3)_2$ or trans-$PtHCl(PMe_3)_2$.

Additional experiments were carried out to determine what effect varying hydroxide-ion concentrations would have on the rate of acetamide production. Table X shows that the rate is nearly linear at low hydroxide-ion concentrations but becomes independent at higher concentrations.

EXAMPLE 5

Catalytic hydration of acetonitrile to acetamide using trans-$NiHCl(P-i-Pr_3)_2$ as catalysts Trans-$NiHCl(P-i-Pr_3)_2$ was prepared as described by Green et al. in the *Journal of the Chemical Society, A*, (1971, 17:152–154). A catalytic solution consisting of 0.02 molar of this substance and one equivalent of NaOH in a solution with equal amounts of acetonitrile and water effected the catalytic hydration of acetonitrile to acetamide at a rate of approximately 21 turnovers/hour at 78° C.

EXAMPLE 6

Catalytic hydration of nitriles containing ester linkages

Ethyldicyanomethylmethylenebutyrate, and methyl-4,4-dicyanobutyrate were converted to 3-cyano-6-hydroxy-2-keto-4-methyl pyridone and 3-cyano-6-hydroxypyridone, respectively, by preparing a catalytic solution under an inert atmosphere of nitrogen containing one equivalent of aqueous NaOH per Pt to water containing the appropriate nitrile. Generally, 0.5 ml of nitrile and 0.5 ml of water were utilized. Approximately 10 mg of the phase-transfer catalyst, $[N(CH_2Ph)Et_3][Cl]$ was present. The reaction was allowed to proceed for 18–24 hours at 78° C., and then the products separated from the catalyst in a two-step process consisting of, first, decomposing the catalyst by opening the reaction vessel and exposing the contents to air (the catalysts are oxygen-sensitive and, hence, readily decompose) and, second, extracting the reaction mixture with hot ethanol and obtaining the desired products by standard recrystallization methods. Table XI shows that methylcyanoacetate is converted to its corresponding amide in the presence of either the $PEt_3$ or the $PMe_3$ analogues. It is apparent from the table that both catalysts are active, with $PMe_3$ exhibiting both a greater rate and extent of conversion.

EXAMPLE 7

Further examples of amide production from nitriles

The nitriles, sec-butyl,t-butylnitrile, 1,1-dicyano-2-methylpent-1-ene, and benzonitrile, were converted to their corresponding amides using the reaction conditions described in Example 4, with the exception that the amide products were separated from the catalyst by exposing the reaction solution to air, followed by extraction of the reaction mixture with diethyl ether. The reaction products were isolated in crystalline form on subsequent cooling of the concentrated ether extracts.

Table XI shows that both catalysts, PEt$_3$ and PMe$_3$, are capable of converting the three nitriles to their corresponding amides but do so with significantly different efficiencies. Most notable is that the PMe$_3$ analogue is capable of nearly complete conversion of the nitriles to their corresponding amides. It is further worth noting that the PEt$_3$ analogue is marginally effective at producing amides from t-butylnitrile. For comparative purposes, Table XI ALSO shows the effect of both catalysts on the production of acetamide from acetonitrile.

EXAMPLE 8

Catalytic hydration of terminal alkenes to primary alcohols with trans-PtHCl(PMe$_3$)$_2$ Representative of the catalytic hydration properties of trans-PtHCl(PMe$_3$)$_2$ is the conversion of 1-hexene to n-hexanol. This can be effected by mixing in a suitable reaction vessel 0.30 ml water, 0.50 ml 12-hexene, 0.20 ml of 1.00 molar aqueous NaOH, 7.7 mg of trans-PtHCl(PMe$_3$)$_2$, and 10 mg of NEt$_3$(CH$_2$Ph)Cl, the latter a phase-transfer catalyst. As the catalytic reaction is air-sensitive, the reaction mixture is deoxygenated and the vessel sealed. The reaction was conducted at 60° C., and the rate of reaction and the reaction products determined. The reaction occurred at a rate of 9.3±0.5 turnovers/hour.

The formation of n-hexanol, as well as other products, was ascertained by gas chromographic techniques or proton nuclear magnetic resonance spectroscopy using standards for comparison. No branched alcohols were detected by gas chromography, and nuclear magnetic resonance spectroscopy of the organic phase revealed that approximately 96% of 1-hexene was converted to n-hexanol. The 96 is a selectivity value and not a yield. Phosphorus-31 nuclear magnetic resonance spectroscopy of the organic and aqueous phases, as well as catalytic activity tests for the two layers, reveal that most catalytic activity resides in the aqueous phase.

EXAMPLE 9

Catalytic conversion of 1-dodecene to n-dodecanol with trans-PtHCl(PMe$_3$)$_2$

The conditions described in Example 8 were similarly employed to convert 1-dodecene to n-dodecanol with the exception that the reaction temperature was 100° C. Again, no branched alcohols were detected.

EXAMPLE 10

Synthesis of 1,4-butanediol from 3-butene-1-ol with trans-PtHCl(PMe$_3$)$_2$ as catalyst A third example exemplifying the production of primary alcohols from alkenes is the generation of 1,4-butanediol from 3-butene-1-ol. The latter is a water-soluble alkene and, therefore, allows for ready determination of the kinetic parameters of the catalytic events. Using the reaction conditions described above for the production of n-hexanol, it was observed that at low alkene concentrations (less than 10% volume), the desired alcohol was produced without significant by-products.

A study of the effects of hydroxide concentration on the rate of hydration of 3-butene-1-ol showed that the reaction was dependent on hydroxide concentration below about 8 equivalents of hydroxide. Above 10 equivalents of hydroxide, the rate of hydration is independent of hydroxide concentration.

The differential dependency of the rate of reaction as a function of hydroxide concentration permits the ready measurement of two rate constants associated with different steps in the catalytic scheme. $k_1$, the rate of displacement of coordinated water by 3-butene-1-ol, was found to be $9.3 \pm 0.5 \times 10^{-3} M^{-1} sec^{-1}$. This step was observed spectroscopically by either $^1$H or $^{31}$P nuclear magnetic resonance techniques. Additionally, $k_2$, or the rate of nucleophilic attack of hydroxide on coordinated 3-butene-1-ol was observed to be $23 \pm 2 M^{-1} sec^{-1}$. The latter therefore appears to be the slow step in the reaction scheme.

EXAMPLE 11

Catalytic hydration of terminal alkenes to primary alcohols with trans-PtHCl(PMe$_3$)$_2$ and the phase-transfer catalyst [NEt$_3$(CH$_2$Ph)][BF$_4$]

The conditions described in Example 8, with the exception that 10 mg of [NEt$_3$(CH$_2$Ph)][BF]$_4$ was substituted for [NEt$_3$(CH$_2$Ph)][Cl] as phase-transfer catalyst, was found to catalyze the selective hydration of 1-hexene to n-hexanol at the rate of 7 turnovers/hour.

TABLE I

Comparison of Catalytic Activities for Hydrolysis of Acetonitrile to Acetamide

| CATALYST | TEMPERATURE °C. | MOLE/MOLE CATALYST h |
|---|---|---|
| trans-[PtHCl(PMe$_3$)$_2$] | 78 | 178.4 |
| trans-[PtHCl(PEt$_3$)$_2$] | 78 | 69.9 |
| trans-Rh(OH)(CO)(PPh$_3$)$_2$ | 80 | 50.0 |
| PdCl(OH)(bipy)(H$_2$O) | 76 | 29.4 |
| Pt[P(c-C$_6$H$_{11}$)$_3$]$_2$ | 80 | 26.7 |
| trans-[PtH(H$_2$O)(PMe$_3$)$_2$][OH] | 25 | 21.5 |
| K$_2$PdCl$_4$, 2,2'-bipyridine, NaOH | 76 | 8.8 |
| Pt(PEt$_3$)$_3$ | 80 | 2.7 |
| NaOH | 78 | 0.4 |

TABLE II

Rate Data for the Hydration of Acetonitrile to Acetamide with PtHCl(PMe$_3$)$_2$ as Catalyst Precursor at 80° C.

| [Pt] (mMole) | H$_2$NC(O)CH$_3$ (mMole h$^{-1}$) |
|---|---|
| .005 | 0.82 |
| .010 | 1.73 |
| .015 | 2.75 |
| .020 | 3.56 |

TABLE III

Rate Data for the Hydration of Acetonitrile to Acetamide with PtHCl(PMe$_3$)$_2$ as Catalyst Precursor and Varied Volume % H$_2$O at 80° C.

| % H$_2$O | Moles Acetamide/Mole Catalyst h |
|---|---|
| 1.2 | 14.7 |
| 2.7 | 23.3 |
| 3.2 | 24.1 |
| 7.7 | 56.0 |
| 31.0 | 154.5 |
| 43.0 | 168.4 |
| 51.7 | 149.3 |
| 71.3 | 115.1 |
| 86.3 | 77.8 |
| 93.4 | 41:6 |
| 94.8 | 40.8 |
| 95.5 | 21.5 |
| 97.8 | 14.8 |
| 99.2 | 7.7 |

TABLE IV

Rate Data for the Hydration of Acetonitrile to Acetamide with PtHCl(PMe$_3$)$_2$ as Catalyst Precursor at Varied Hydroxide Concentrations at 80° C.

| [OH] (μM) | Moles Acetamide/Mole Catalyst h |
|---|---|
| 0.1 | 2.3 |
| 0.3 | 7.5 |
| 1.0 | 31.1 |
| 3.2 | 80.2 |
| 4.0 | 100.4 |
| 5.0 | 129.5 |
| 6.3 | 153.0 |
| 10.0 | 178.0 |

TABLE V

Rate Data for the Hydration of Acetonitrile to Acetamide with PtHCl(PMe$_3$)$_2$ as Catalyst Precursor at 80° C.

| Time (h) | Moles Acetamide/Mole Catalyst |
|---|---|
| 6 | 2.2 |
| 20 | 6.2 |
| 60 | 19.9 |
| 240 | 85.8 |

TABLE VI

Rate and Product Distribution Data for the Hydration of Acrylonitrile with PtHCl(PMe$_3$)$_2$ as Catalyst Precursor and Varied Hydroxide Concentration at 80° C.

| OH (mM) | Moles acrylamide/Mole Catalyst h | Moles beta-cyanoethanol/Mole Catalyst h | Moles di-cyanoethyl ether/Mole Catalyst h | Total Moles C=C hydrated/Mole Catalyst h |
|---|---|---|---|---|
| .01 | 57.3 | 40.0 | 34.1 | 74.1 |
| .02 | 67.9 | 72.5 | 66.9 | 139.4 |
| .04 | 61.6 | 167.2 | 174.1 | 341.3 |
| .06 | 71.4 | 184.9 | 235.3 | 420.2 |

TABLE VII

Rate and Product Distribution Data for the Hydration of Acrylonitrile with PtHCl(PMe$_3$)$_2$ as Catalyst Precursor and Varied Volume % H$_2$O at 80° C.

| % H$_2$O | Moles acrylamide/Mole Catalyst h | Moles beta-cyanoethanol/Mole Catalyst h | Moles di-cyanoethyl ether/Mole Catalyst h | Total Moles C=C hydrated/Mole Catalyst h |
|---|---|---|---|---|
| 90 | 9.4 | 29.1 | 7.7 | 36.8 |
| 80 | 28.0 | 62.8 | 29.9 | 92.7 |
| 70 | 39.6 | 81.8 | 44.5 | 126.3 |
| 60 | 50.4 | 75.8 | 51.9 | 127.7 |
| 50 | 65.0 | 66.0 | 56.2 | 122.2 |
| 40 | 68.2 | 53.0 | 55.2 | 108.2 |
| 30 | 53.8 | 38.8 | 48.7 | 88.5 |
| 20 | 38.4 | 14.5 | 30.0 | 54.5 |
| 10 | 22.8 | 12.8 | 18.4 | 31.2 |

TABLE VIII

Comparison of Catalytic Activities and Product Distribution for Hydrolysis of Acrylonitrile

| Catalyst | Temperature °C. | Moles/Mole Catalyst h | | | Hydrolysis C≡N/C=C |
|---|---|---|---|---|---|
| | | CH$_2$=CHC(O)NH$_2$ | HOCH$_2$CH—C≡N | (N≡CCH$_2$CH$_2$)$_2$O | |
| PtHCl(PMe$_3$) | 25 | 6.20 | 0.02 | 0.19 | 29.52 |
| PtHCl(PMe$_3$) | 80 | 65.00 | 84.50 | 10.50 | 0.41 |

TABLE IX

Rate Data for the Hydration of Acetonitrile to Acetamide with PtHCl(PEt$_3$)$_2$ as Catalyst Precursor with Varied Added PEt$_3$ at 80° C.

| Equivalents PEt$_3$ | 1/Moles Acetamide/Mole Catalyst h$^{-1}$ |
|---|---|
| 0 | 0.014 |
| 0.25 | 0.019 |
| 0.50 | 0.026 |
| 0.75 | 0.029 |
| 1.00 | 0.036 |
| 2.00 | 0.058 |

TABLE X

Rate Data for the Hydration of Acetonitrile to Acetamide with PtHCl(PEt$_3$)$_2$ as Catalyst Precursor at Varied Hydroxide Concentrations at 80° C.

| [OH] (μM) | Moles Acetamide/Mole Catalyst h |
|---|---|
| 0.1 | 1.5 |
| 0.3 | 4.4 |
| 1.0 | 15.0 |
| 2.0 | 36.7 |
| 2.5 | 45.4 |
| 3.2 | 55.4 |
| 4.0 | 67.8 |
| 10.0 | 69.2 |
| 31.6 | 69.8 |

TABLE XI

Catalytic Rates and Extent Conversions for Hydration of Nitriles Catalyzed by PtHClL$_2$ (L=PEt$_3$ and PMe$_3$) at 78° C.

| | PtHCl(PEt$_3$)$_2$ | | PtHCl(PMe$_3$)$_2$ | |
|---|---|---|---|---|
| Nitrile | Mole/Mole Catalyst h | Maximum % Conversion[a] | Mole/Mole Catalyst h | Maximum % Conversion[b] |
| CH$_3$C≡N | 70 | 98 | 178 | >98 |
| Me$_2$CHC≡N | 17 | >98 | 113 | >98 |
| Me$_3$CC≡N | <1 | <1 | 10 | >98 |
| PhC≡N | 5 | >98 | 10 | >98 |
| MeOC(O)CH$_2$C≡N | 4 | 91[c] | 7 | 94[d] |
| (N≡C)$_2$C=C(Me)CH$_2$$\overset{O}{\overset{\|}{C}}$OEt | 9 | 40 | 22 | 88 |
| (N≡C)$_2$C=C(Me)(Pr) | | | 15 | 64 |

TABLE XI-continued

Catalytic Rates and Extent Conversions for
Hydration of Nitriles Catalyzed by $PtHClL_2$
($L=PEt_3$ and $PMe_3$) at 78° C.

| Nitrile | PtHCl(PEt$_3$)$_2$ | | PtHCl(PMe$_3$)$_2$ | |
|---|---|---|---|---|
| | Mole/Mole Catalyst h | Maximum % Conversion[a] | Mole/Mole Catalyst h | Maximum % Conversion[b] |
| (N≡C)$_2$CHC$_2$H$_4$COMe | | | 25 | 72 |

[a]24 h reaction time. For all nitriles < 3% conversion occurred if the NaOH was added without the platinum catalyst.
[b]18 h reaction time.
[c]95% selective for methylacetamidate vs. cyanoacetic acid.
[d]97% selective for methylacetamidate vs. cyanoacetic acid.

We claim:

1. A method of hydrating olefinic linkages in a compound via anti-Markownikoff addition comprising admixing in an oxygen-free solution the following reactants: water, a compound exhibiting an olefinic linkage, hydroxide ions, PtHCl(PMe$_3$)$_2$, a phase-transfer catalyst, and allowing said reactants to interact at 25° C.–100° C. for a time sufficient to effect said hydration.

2. A method as described in claim 1 wherein said compound containing said olefinic linkage is an alkene.

3. A catalytic solution useful for hydrating olefinic linkages via anti-Markownikoff addition comprising a compound exhibiting an olefinic linkage, water, a nucleophile, and trans-PtHCl(PMe$_3$)$_2$.

4. A catalytic solution as described in claim 3 wherein said compound is an alkene, and said alkene being hydrated to a primary alcohol.

5. A catalytic solution as described in claim 3 wherein said nucleophile is hydroxide ion.

6. A catalytic solution as described in claim 3 wherein said catalytic solution contains a phase-transfer catalyst.

7. A catalytic solution as described in claim 6 wherein the phase-transfer catalyst is drawn from the group consisting of [NEt$_3$(CH$_2$Ph)][Cl] and [NEt$_3$(CH$_2$Ph)][BF$_4$].

* * * * *